US008029726B2

(12) United States Patent
Resch et al.

(10) Patent No.: US 8,029,726 B2

(45) Date of Patent: Oct. 4, 2011

(54) DISINFECTION METHODS FOR SURFACES AND ENCLOSED SPACES

(75) Inventors: Darrel R. Resch, Orlando, FL (US); Griscom Bettle, III, Sarasota, FL (US)

(73) Assignee: .Vapex Technologies, Inc., Orlando, FL (US)

( * ) Notice: Subject to any disclaimer, the term of this patent is extended or adjusted under 35 U.S.C. 154(b) by 644 days.

(21) Appl. No.: 12/125,427

(22) Filed: May 22, 2008

(65) Prior Publication Data

US 2008/0292498 A1 Nov. 27, 2008

Related U.S. Application Data

(60) Provisional application No. 60/939,402, filed on May 22, 2007.

(51) Int. Cl.
*A61L 2/20* (2006.01)

(52) U.S. Cl. .......................................... 422/28; 239/398

(58) Field of Classification Search ................ 422/4, 28, 422/29; 239/398

See application file for complete search history.

(56) References Cited

U.S. PATENT DOCUMENTS

| | | | |
|---|---|---|---|
| 1,594,947 | A | 8/1926 | Hartman et al. |
| 2,388,753 | A | 11/1945 | Mallmann et al. |
| 4,196,726 | A | 4/1980 | Ronzi |
| 5,246,556 | A | 9/1993 | Sawamoto et al. |
| 5,337,962 | A | 8/1994 | Erb et al. |
| 5,344,622 | A | 9/1994 | Faddis et al. |
| 5,431,861 | A | 7/1995 | Nagahiro et al. |
| 5,882,591 | A | 3/1999 | Kekez |
| 5,931,014 | A | 8/1999 | Cole |
| 5,951,921 | A | 9/1999 | Koganezawa et al. |
| 6,029,911 | A | 2/2000 | Watanabe et al. |
| 6,076,748 | A | 6/2000 | Resch et al. |
| 6,231,648 | B1 | 5/2001 | Marlowe |
| 6,287,465 | B1 | 9/2001 | Watanabe et al. |

(Continued)

FOREIGN PATENT DOCUMENTS

JP 01032866 2/1989

(Continued)

OTHER PUBLICATIONS

Bioquell™ Z and Clarus™ C, product information, [online], [retrieved on Jun. 18, 2008], Retrieved from the Drug Development Technology website using Internet <URL:http://www.drugdevelopment-technology.com/company_printable.asp?ProductSubGroupID=1742&CompanyID=32764>.

(Continued)

*Primary Examiner* — Sean E Conley

(74) *Attorney, Agent, or Firm* — Allen Dyer Doppelt Milbrath & Gilchrist

(57) ABSTRACT

A system and method for producing an ozone-containing disinfecting cloud includes an enclosure. A pair of atomizing nozzles are affixed to the enclosure in substantially directly opposed relation. Each nozzle produces a spray of ozonated water from compressed gas, ozone, and water and are positioned to direct the sprays toward each other to form a cloud comprising droplets having a size distribution. A portion of the cloud that comprises droplets having a size less than a predetermined limit is expelled from the enclosure. Droplets having a size greater than the predetermined limit remain in the enclosure. The expelled cloud has been found to have a pH lower than a pH of the remaining droplets. The cloud so produced can be used to disinfect an area by directing the cloud to the area desired to be disinfected, which can comprise a surface and/or a space.

8 Claims, 5 Drawing Sheets

U.S. PATENT DOCUMENTS

| | | | |
|---|---|---|---|
| 6,537,494 | B2 | 3/2003 | Garlick |
| 6,648,307 | B2 | 11/2003 | Nelson et al. |
| 6,817,541 | B2 | 11/2004 | Sands et al. |
| 7,014,813 | B1 | 3/2006 | Watling et al. |
| 2002/0011253 | A1 | 1/2002 | Puri et al. |
| 2004/0096354 | A1 | 5/2004 | Nomura et al. |
| 2004/0154328 | A1 | 8/2004 | Holtzapple et al. |
| 2006/0005861 | A1 | 1/2006 | Lynn |
| 2006/0107976 | A1 | 5/2006 | Boyers et al. |
| 2006/0140817 | A1 | 6/2006 | Cumberland et al. |
| 2006/0144700 | A1 | 7/2006 | Carson et al. |
| 2007/0086913 | A1 | 4/2007 | Teran et al. |
| 2007/0205161 | A1 | 9/2007 | Chiba et al. |
| 2007/0261716 | A1 | 11/2007 | Franklin et al. |
| 2007/0295021 | A1 | 12/2007 | Tyls et al. |

FOREIGN PATENT DOCUMENTS

| | | |
|---|---|---|
| JP | 04243518 | 8/1992 |
| JP | 08238490 | 9/1996 |
| JP | 11114390 | 4/1999 |
| JP | 2000316956 | 11/2000 |
| JP | 2002079192 | 3/2002 |
| JP | 2003320278 | 11/2003 |
| JP | 2004173904 | 6/2004 |
| WO | 2005115553 | 12/2005 |

OTHER PUBLICATIONS

Kowalski et al., "Demonstration of a Hermetic Airborne Ozone Disinfection System: Studies on *E. coli*," AIHA Journal, No. 64, pp. 222-227, Mar./Apr. 2003.

DISINFECTION METHODS FOR SURFACES AND ENCLOSED SPACES

CROSS-REFERENCE TO RELATED APPLICATION

This application claims priority to provisional application Ser. No. 60/939,402, filed May 22, 2007.

BACKGROUND OF THE INVENTION

1. Field of the Invention

This invention is directed to disinfection systems and methods, and, more particularly, to such disinfection systems and methods that produce and utilize a mist comprising ozone and other reaction products.

2. Related Art

Ozone is an unstable molecule consisting of three oxygen atoms. An ozone molecule will naturally decay to a single oxygen atom and an oxygen molecule containing two oxygen atoms. If the single oxygen atom does not come into contact with another single oxygen atom and merge with it to form an oxygen molecule, the single oxygen atom will oxidize any inorganic molecule that it comes into contact with and any organic molecule that is susceptible to oxidation that it comes into contact with.

Ozone's half-life in air due to thermal decay at room temperature is about three days; in clean water, the half-life is about 30 min. In practical applications, however, the half-life is much less because of wall effects, humidity, organic loading, and catalytic reactions. Because it is unstable, with a short half-life, ozone must be generated where it is to be used. Ozone may be generated by exposing dry oxygen or a dry gas containing oxygen, such as air, to ultraviolet light, or a high voltage electric field that is corona discharging at the surface of the conductors.

Exposing a surface that is contaminated with one or more biological contaminants, such as bacteria, virus, fungus, fungus spores, yeast, and/or other microorganisms, to ozone will disinfect the surface. Likewise, exposing a confined gas, such as air, that contains biological contaminants to ozone will disinfect the gas. This is because ozone, upon coming into contact with a biological contaminant, initially oxidizes the sheath of the biological contaminant, thereby inactivating it. If the oxidization process continues to completion, the ozone will typically convert the biological contaminant to essentially harmless byproducts, such as water and carbon dioxide. This is an advantageous method for sterilizing a surface or a gas because the process is simple and the end products of the oxidization, water and carbon dioxide, and the end product of the ozone decay, molecular oxygen, are harmless.

The principal difficulties with using ozone to disinfect a surface or a gas are: (1) only weak concentrations of ozone may be achieved in a practical application of ozone to a surface or a volume of gas because of ozone's short half-life in practical applications, and (2) ozone is injurious to humans at the concentrations required to disinfect a surface or a gas. The consequences of the foregoing are that in order to disinfect a surface or a gas with ozone: (a) the surface or the gas to be disinfected must be in an enclosed space, which means the disinfection process must be a batch process, not a continuous process, (b) the disinfection process will require significant time, (c) unprotected humans may not be present in the enclosed space during the disinfection process, and (d) the gases venting from the enclosed space during the disinfection process and at the end of the process must be passed through a catalytic converter or some other means that removes any residual ozone in the exhaust gas.

According to an article titled "Demonstration of a Hermetic Airborne Ozone Disinfection System Studies on *E. coli*" published in the March/April 2003 issue of the American Industrial Hygiene Association, a six-log (base 10) reduction in a microbial population (the common definition of sterilization) can be achieved by exposing a microbial population to 1 to 3 parts per million of ozone for four hours. The U.S. Occupational Safety and Health Administration (OSHA) has set the Public Health Air Standard limit for exposure to 0.1 parts per million of ozone at eight hours and to 15 minutes for exposure to 0.3 parts per million of ozone. Because of the foregoing limitations, it has not been practical to disinfect a surface or a gas with ozone.

Ozone is slightly soluble in water, and, when dissolved in water, will quickly decompose to form the free radicals hydroxide (OH.) and hydrogen dioxide ($HO_2$.) which in turn form hydrogen peroxide ($H_2O_2$). Hoigne described the hydroxyl free radical chemistry as having three steps: initiation, propagation, and termination. In initiation, free radicals are produced by ozone decomposition. In propagation, oxygen and water are made into free radicals by the initiating radical. In termination, the free radicals are absorbed, and the reaction stops. The propagation chemistry is very complex and hard to measure and is modified by changes in the water chemistry and the gas chemistry. The initiation chemistry is more straightforward, and scientists agree that the chemistry is:

$$O_3+OH^- \rightarrow O_2.^- +HO_2. \qquad 1.$$

which indicates the formation of a superoxide radical and a hydroperoxyl radical from ozone;

$$HO_2. \rightarrow O_2.^- +H^+, pK_a=4.8 \qquad 2.$$

which indicates the formation of a superoxide radical. Together, it is obvious that the initiation reactions consume hydroxyl ions and produce protons, a pH-lowering chemistry. If a droplet of ozone and water dropped in pH, it would indirectly indicate that the hydroxyl free radical chemistry had been initiated.

There may be other reactions and reaction end products from putting ozone into water solution, depending on the pH of the water and whether other chemicals are present in the water. Both hydroxide and hydrogen dioxide are strong oxidizers, and each will oxidize any inorganic molecule and any organic molecule that is susceptible to oxidation with which it comes into contact. This is one reason ozone is increasingly being used by public water supply systems as a disinfectant, and also a reason ozonated water is increasing being used as a disinfectant wash for foods, such as fruits, vegetables, and poultry. 21 Code of Federal Regulations 173, Part D, Subsection 173.368 states that ozone may safely be used for the treatment, storage, and processing of foods, including meat and poultry.

The chemistry of ozone-initiated free radicals is very complex. Ozone-initiated free radicals are Nature's way of cleaning up the upper atmosphere (above visible clouds). Ultraviolet (uv) light from the sun converts oxygen into ozone. The ozone is dissolved in <1 μm water droplets along with volatile pollutants. The surface tension of a droplet increases the pressure inside the droplet (P=($2^{72}$ dyn/cm)/droplet radius). A 1-μm diameter droplet has an internal pressure at sea level of ~70 psia; a 0.5-μm diameter droplet has an internal pressure of 140 psia. At these very high pressures, the light-induced ozone is converted into a variety of free radicals that clean the atmosphere.

The term "ozonated water" is used herein to refer to water containing the end products of the chemical reaction of ozone with water. The composition of the end products will vary depending on several factors, principally the pH of the water and whether the water contains other dissolved chemical compounds.

If ozone were highly soluble in water, one could easily disinfect a surface by simply dissolving ozone into water to a sufficiently high concentration, allowing the ozone to react with the water to form hydroxide, hydrogen dioxide, and other free radical reaction products and then spraying or swabbing the ozonated water onto the surface and one could disinfect a gas by simply spraying the ozonated water into the gas as a fine mist. The ozonated water, if allowed to wet the biological contaminants on the surface or floating in the gas for a sufficiently long time, will first oxidize the outer surface of the contaminants, thereby killing the biological contaminants, and, if the biological contaminates are exposed to the ozonated water for a sufficiently long time, the ozonated water will eventually oxidize the biological contaminants, thereby eliminating them.

Because ozone is not readily soluble in water, however, simply bubbling ozone through a water column will not result in sufficient ozone being absorbed into the water to produce hydroxide and hydrogen dioxide and other free radical reaction end products at a sufficient concentration for disinfection purposes other than the disinfection of the water itself.

One of the present inventors has described a three-fluid nozzle that uses compressed air as a motive force, a low pressure side stream of ozone gas, and a thin film of water to make fine droplets (Resch et al., U.S. Pat. Nos. 6,076,748 and 5,337,962, both of which are incorporated hereinto by reference). The '748 patent teaches that the water is stretched into ribbons, the ribbons increasing the solubility of ozone in the water, with the ribbons then fragmenting into droplets. There is considerable droplet size distribution, with the number median diameter about 3 μm. The mass median diameter is an order of magnitude larger, indicating the presence of very large particles in the distribution.

Another of the present inventors has disclosed a method of making very small bubbles in water (Bettle, U.S. Pat. No. 5,772,886). The '886 patent teaches that impinging a contained gas/liquid stream against another contained gas/liquid stream at combined velocities greater than 7 ft/sec fractionates the bubbles to less than 1 μm. Extremely small bubbles do not float out of the surrounding water.

It has been reported by Cho ("Disinfection of Water Containing Natural Organic Matter by Using Ozone-initiated Radical Reactions" (*Appl. Environ. Microbiol.,* 2003 April; 2284-2291) that the CT (concentration*time) "value of hydroxyl radicals for a two-log reduction of *B. subtilis* was estimated to be about $2.4\times10^4$ times smaller than that of ozone and was $10^6$ and $10^5$ times lower than those of free chlorine and chlorine dioxide, respectively." Thus Cho teaches that hydroxyl radicals are many orders of magnitude faster disinfectants than ozone, chlorine, and chlorine dioxide.

Owing to a well-known need to disinfect a plurality of areas of the environment, it would therefore be advantageous to provide a high-concentration composition comprising free radicals for disinfection purposes, and a method of making same. It would also be advantageous to provide such a composition in a mist form, and preferably in a form that does not substantially wet contacted surfaces.

SUMMARY OF THE INVENTION

The present invention is directed to a system and method for producing an ozone-containing disinfecting cloud, to the cloud so produced, and to a method of disinfecting an area. The area can comprise, for example, a three-dimensional space and the surfaces within the space.

The system comprises an enclosure. A pair of atomizing nozzles are affixed to the enclosure in substantially directly opposed relation. Each nozzle is adapted to produce a spray of ozonated water from input compressed gas, ozone, and water. The pair of atomizing nozzles are positioned so as to direct the produced sprays from outlets thereof toward each other to form a cloud comprising droplets having a size distribution.

An air-moving device is affixed to the enclosure for expelling therefrom a portion of the cloud that comprises droplets having a size less than a predetermined limit found to be effective in disinfection. Substantially all the droplets having a size greater than the predetermined limit remain in the enclosure. The expelled cloud has been found to have a pH lower than a pH of the remaining droplets.

The cloud so produced can be used to disinfect an area by directing the cloud to the area desired to be disinfected, which can comprise a surface and/or a space.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWING

FIGS. 4A-4C are schematic diagrams of the impingement characteristics of droplets with three nozzle spacings, 12 in. (FIG. 4A), 24 in. (FIG. 4B), and 36 in. (FIG. 4C).

DETAILED DESCRIPTION OF THE PREFERRED EMBODIMENT

Figure 1A:
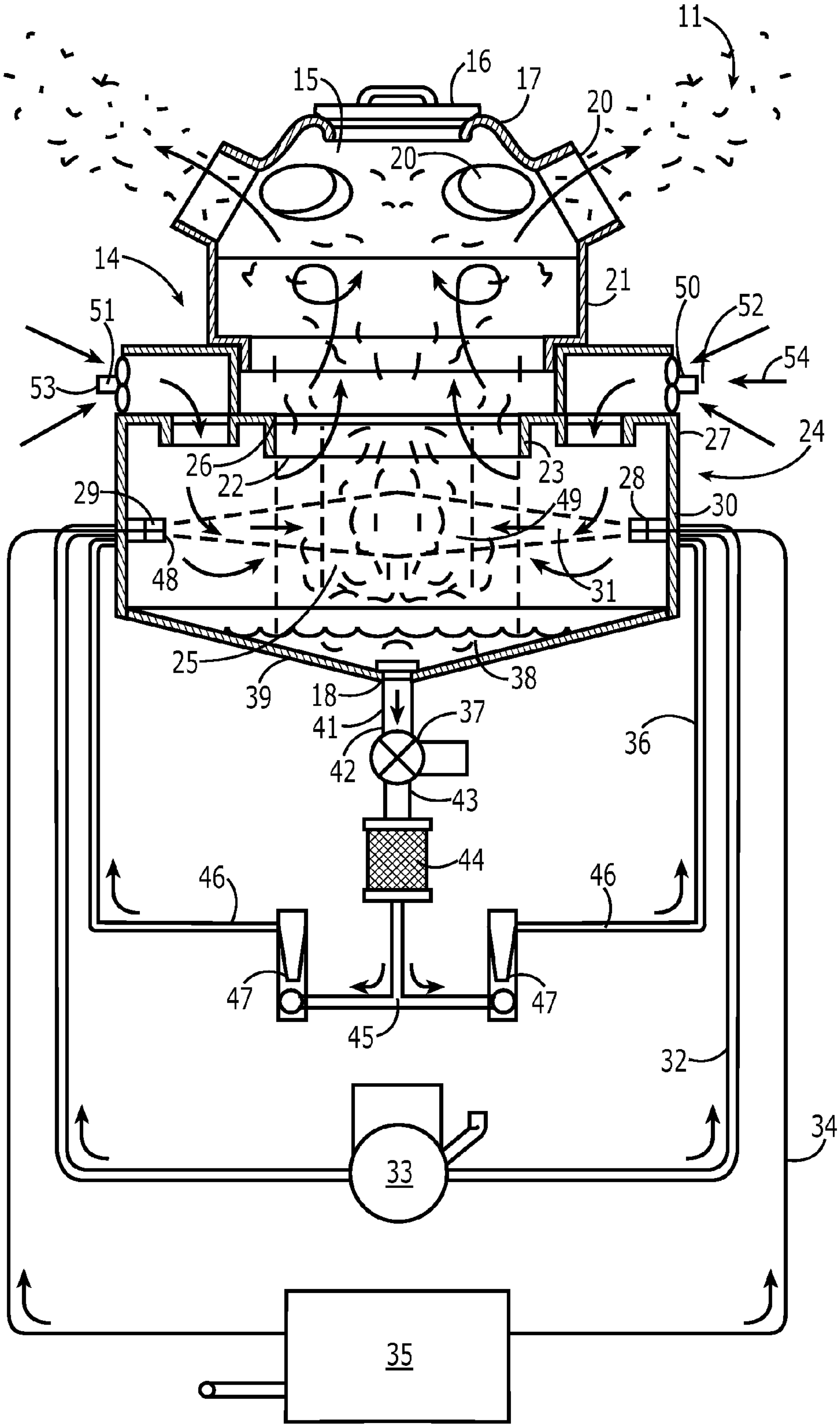
FIG. 1A is a schematic cross-sectional view of the disinfecting-mist-generation system of the present invention.
Figure 1B:
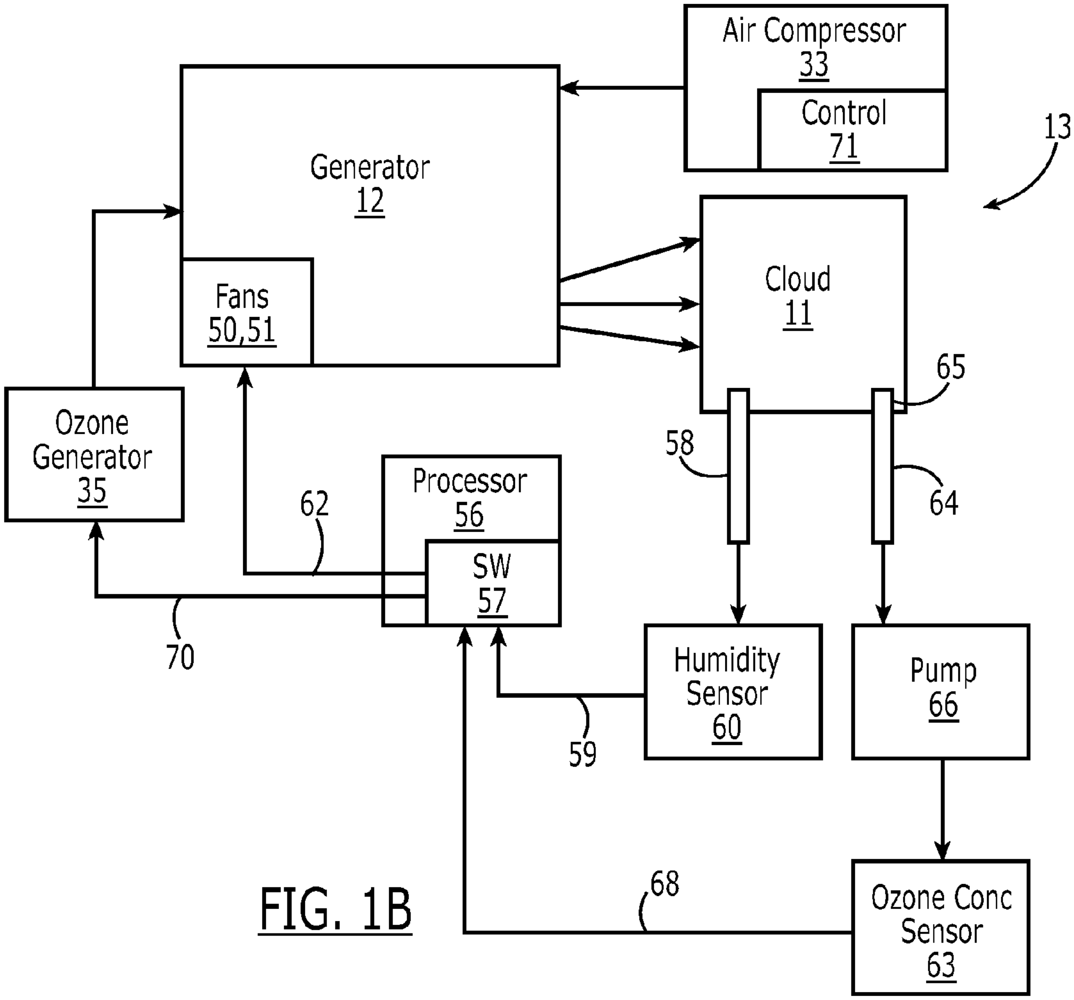
FIG. 1B is a schematic diagram of the measurement and control system for use with the system of FIG. 1A.

A description of the preferred embodiments of the present invention will now be presented with reference to FIGS. 1A-4.

The system 10 for producing an ozone-containing disinfecting cloud 11 comprises a generator 12 (FIG. 1A) and a control system 13 (FIG. 1B) for controlling various aspects of the generator 12.

The generator 12 comprises an enclosure 14 having an inlet 15 with a removable cap 16 at a top end 17, a water outlet 18 at a bottom end 19, and a plurality of radially spaced-apart cloud outlets 20 adjacent the top end 17. An exemplary number of cloud outlets is six, although this is not intended as a limitation. A top portion 21 of the enclosure 14 can be substantially dome-shaped with an opening 22 at a bottom end 23, and with the cloud outlets 20 projecting upwardly and outwardly therefrom, although this is not intended as a limitation.

A lower portion 24 of the enclosure 14 can comprise an "impaction vessel," wherein an ozonated cloud 25 is created. The enclosure's lower portion 24 has an opening 26 at a top end 27 into which the top portion's bottom end 23 is insertable for fluid communication therebetween.

A pair of atomizing nozzles 28,29 (Model #500, Vapex, Inc., Orlando, Fla.) are affixed through a wall 30 of the enclosure's lower portion 24 in substantially directly opposed relation. The atomizing nozzles 28,29 can comprise those such as taught in the above-cited '748 and '962 patents, although this is not intended as a limitation. Each of the nozzles 28,29 is adapted for producing a spray 31 of ozonated water from input comprising compressed air piped 32 from an air compressor 33, ozone piped 34 from an ozone generator 35, and water piped 36 from a water circulation pump 37. The water is obtained from two sources: condensate 38 from the ozonated cloud 25, and supply water added via the enclosure's top inlet 15. The water from both sources collects at a bottom 39 of the enclosure's lower portion 24, which has a tapered shape toward the bottom outlet 18 in fluid communication via piping 41 to the water circulation pump inlet 42. Water exiting the water circulation pump outlet 43 proceeds through a water filter 44 to a "T" junction 45 that splits the water flow into two channels 46 leading to a respective one of the nozzles 28,29 via a rotameter 47 that controls flow.

The pair of atomizing nozzles 28,29 are arranged so as to direct the produced sprays 31 from outlets 48 thereof toward each other within an impingement zone 49, to form the cloud 25 comprising droplets having a size distribution. In an exemplary embodiment, the sprays 31 emerge from the nozzles 28,29 at approximately 300 mph, although this is not intended as a limitation.

A pair of fans 50,51 are affixed to the enclosure's lower portion 24, one above each of the nozzles 28,29, through airflow inlets 52,53 for directing airflow 54 from exterior the enclosure 14 toward the nozzles' outlets 48. The airflow 54 acts to expel a portion 11 of the formed cloud 25 containing droplets having a size less than a predetermined limit, for example, less than 1 μm, although this is not intended as a limitation. Droplets having a size greater than the predetermined limit condense and remain in the enclosure's lower portion 24 as condensate 38. Optionally, the fans 50,51 can be eliminated, and natural convection and gas flow control elements can be used to move droplets into the space.

A control system 13 for controlling various aspects and parameters of the generator 12 (FIG. 1B) includes a processor 56 having software 57 resident thereon for performing calculations and issuing control signals. A humidity sensor probe 58 is positionable within the expelled cloud 11 that is in signal communication 59 with the processor 56 via a sensor apparatus 60. The fans 50,51 have resident therein a fan-speed controller in signal communication 62 with the processor 56. The software 57 can receive a measurement of humidity from the humidity sensor 60 and compare it with a predetermined humidity value. The software 57 can then issue a control signal 62 signaling the fan-speed controller to increase the fan speed if the received humidity measurement is less than the predetermined humidity value, or to decrease the fan speed if the received humidity measurement is greater than the predetermined humidity value.

The humidity value is preferably less than 100% relative humidity (RH), for example, in a range of 70-99%, and most preferably in a range of 85-95%. If the RH is above 100%, the area is wetted; below 70% RH, the droplets can evaporate.

The control system 13 further comprises an ozone-concentration sensor 63 comprising a sample tube 64 having an outlet 65 positionable in the expelled cloud 11 and an outlet through a pump 66 to an ozone sensor 67 in signal communication 68 with the processor 56. The software 57 can receive a measurement of ozone concentration in the expelled cloud 11 from the sensor 63, for comparing the received ozone concentration measurement with a predetermined concentration value. The software 57 can issue a signal 70 to the ozone generator 35 to increase the generated ozone if the received concentration measurement is less than the predetermined concentration value, or to decrease the generated ozone if the received concentration measurement is greater than the predetermined concentration value.

The control system 13 additionally comprises a control feature 71 in the air compressor 33 for controlling the velocity of the spray 31 produced by the nozzles 28,29, which will affect the droplet size distribution in the cloud 25.

The operation of the system 10 and results obtained therewith will now be discussed. It has been found that, when the spray 31 from the two nozzles 28,29 directly impinge on one another in the confined space 72 of the enclosure 14, a bimodal distribution of droplet diameters is created, one of droplets<1 μm, and the other with droplets large enough to sink rapidly. The large-diameter droplets are captured in the enclosure 14 as described above. Small and intermediate droplets, representing approximately 13% of all the droplets formed, can escape via the cloud outlets 20. If any intermediate-sized droplets escape, they evaporate and dissipate.

It has been found that, surprisingly, water in the <1-μm droplets is not as volatile as water in droplets>1 μm. The small droplets survive as a light-scattering cloud; the intermediate droplets evaporate in the <100% RH environment.

Figure 2:
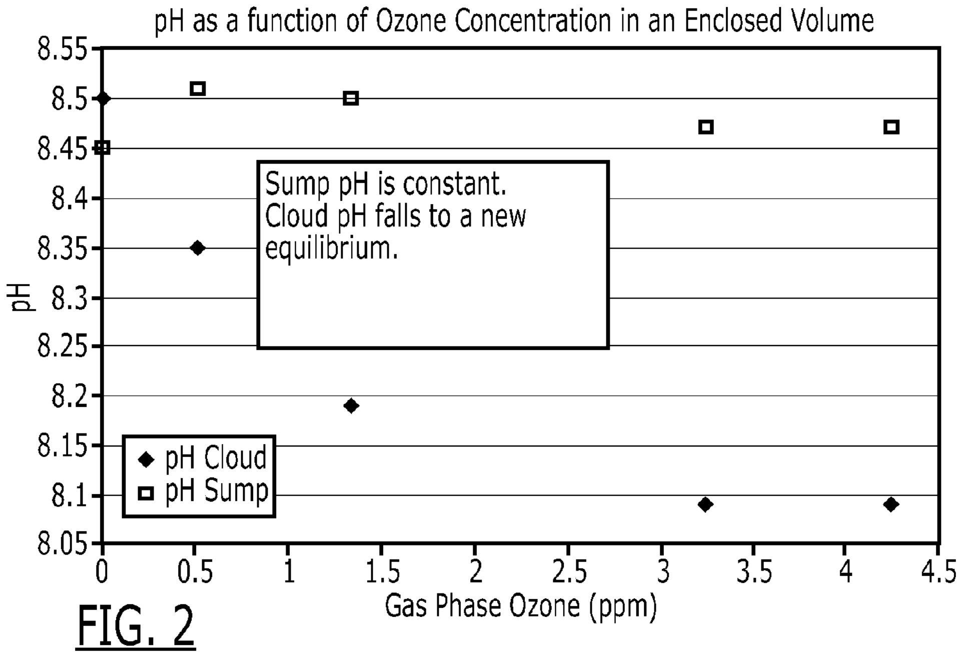
FIG. 2 is a graph of pH as a function of gas-phase ozone concentration in an enclosed volume.
Figure 3A:
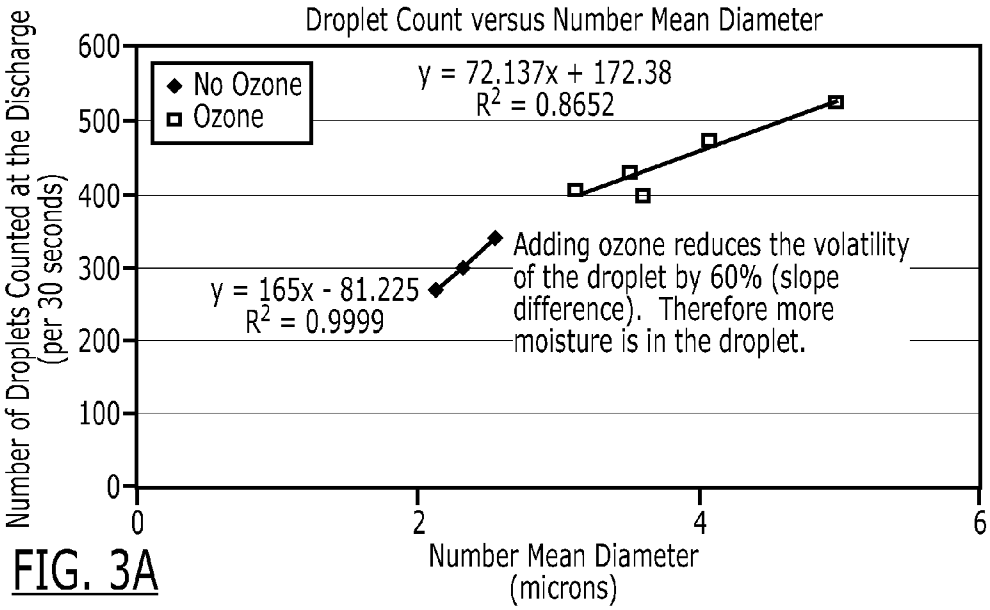
FIG. 3A is a graph of droplet count versus number mean diameter without (♦) and with (□) ozone.
Figure 3B:
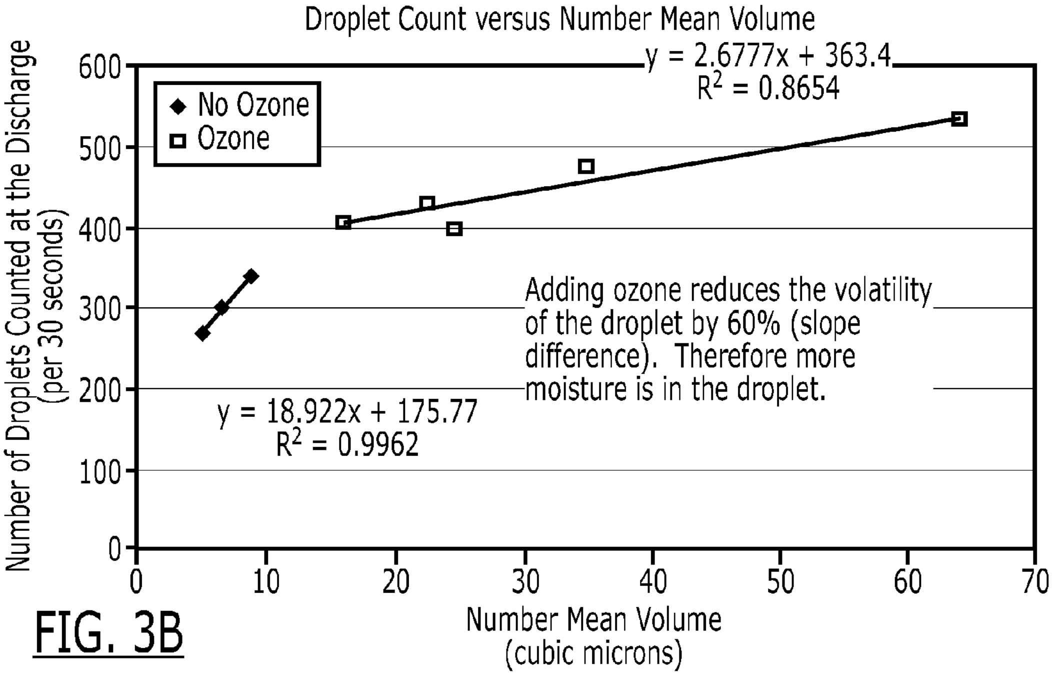
FIG. 3B is a graph of droplet count versus number mean volume without (♦) and with (□) ozone.
Figure 4A:
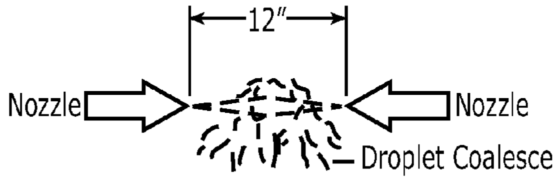
Figure 4B:
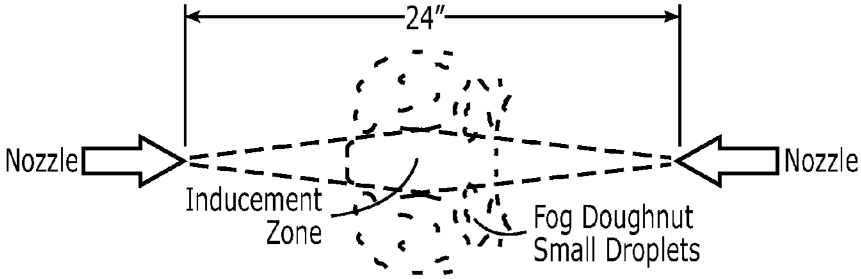
Figure 4C:
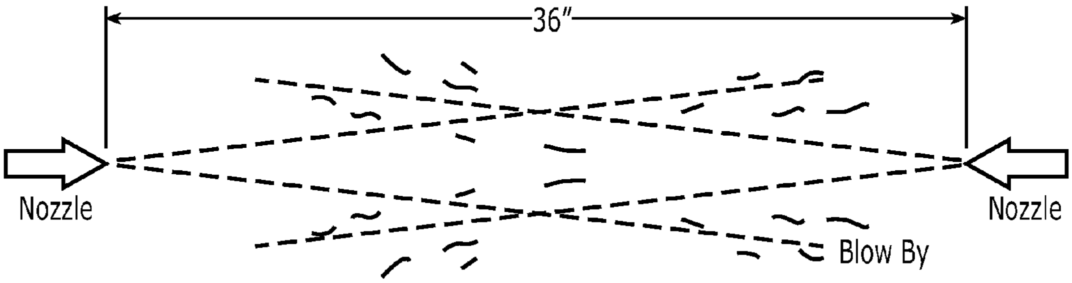

The pH of water used to form droplets is unchanged when large droplets coalesce and are collected in the enclosure 14 ("sump"; FIG. 2). The RH was controlled at 93%; the pH of the enclosure water 38 was measured directly, and the pH of the cloud 11 was measured 2 ft from the centerline of the cloud outlet 20. Surprisingly, the pH of the nonvolatile small droplets falls ("cloud") to a new equilibrium. The disinfecting power is maximized when the ozone dose (at >3 ppm) is sufficient to drop the pH to a new lower equilibrium.

Without wishing to be bound, it is believed that ozone is dissolved in water to form droplets, as taught in the cited '748 and '962 patents to Resch et al. When the sprays 31 from the two nozzles 28,29 impinge on one another, there exists a colliding velocity that fractionates some of the droplets and coalesces some of the droplets, analogous to the teachings of the '886 patent to Bettle. At too high a velocity, the coalescing is excessive; at too low a velocity, fractionating does not occur. As stated above, the confined space 72 collects the large droplets in a pool 38; small and intermediate droplets escape 11. The fraction that escapes is a function of the volume of air moving through the confined space 72. This is controlled by the fans' being logically slaved to the relative humidity measuring device 59.

Smaller droplets have higher internal pressure than larger droplets. At a pressure≧4 atm (~1-μm diameter), the free radical propagation reactions are thermodynamically possible, and the droplet pH drops due to initiation of the propagating hydroxyl free radical cascade. Using unknown mechanisms, these droplets are less volatile than droplets of water alone. Lower-pressure droplets evaporate; higher-pressure droplets survive. The higher-pressure droplets cannot be seen with the naked eye, nor can they be measured with droplet measuring devices, but they can be seen when illuminated by light, as they reflect light much as smoke and or dust does.

These small droplets move about the enclosed space by Brownian motion and air currents from the fans 50,51. As taught by Cho, these droplets are 4 orders of magnitude faster at disinfecting than ozone alone. Gas-like particles move into crevices and hidden places, allowing disinfection of non-uniform surfaces such as the surface of fruits and vegetables without wetting the surfaces. The small droplets are surprisingly long lasting and thus effective for a long time at low doses even though the concentration is very low.

It is unexpected that a ozone/water cloud 11 can be formed where the cloud pH is less than the pH of the water used to form the cloud 11 and less than the pH of the cloud-generating condensate, and the volatility of the cloud 11 is constrained such that the relative humidity can be controlled at <100% and light-scattering droplets remain distributed throughout the enclosed space. The cloud 11 itself is relatively "dry," and disinfected surfaces are not substantially wetted.

The system 10 was operated at a RH<100% at various ozone settings, including zero ozone. The number of droplets captured after 30 sec was measured at a cloud outlet 20 and 5 ft from the cloud outlet 20 along the centerline. The instrument also determines the median droplet diameter, mass, and volume. The results are plotted in FIG. 3A, wherein droplet count is plotted versus number mean diameter, and in FIG. 3B, wherein droplet count is plotted versus number mean volume. A slope of the curve is an indirect measure of the volatility of the droplets, and it is shown that adding ozone reduces the volatility of the droplets by 60%. Therefore, there is less moisture lost from the droplets. The curve for no ozone is clearly steeper than that for the ozone-containing droplets. No droplets were measured 5 ft from the cloud outlet 20. When a bright light was shined at the 5-ft level, there were no reflected droplets in the no-ozone trial; visible cloud 11 was observed in the with-ozone trial.

The number median diameter is determined instrumentally along with the droplet count. The median diameter was used to calculate the volume of the hypothetical median droplet. Droplet count was closely predicted by number mean volume (no ozone, $R^2$=0.9962; with ozone, $R^2$=0.8654]. The slope of the no-ozone curve is 7 times steeper than the slope of the with-ozone curve. A steep slope indicates that the number of droplets counted falls as the diameter falls. This is consistent with rapid evaporation in a RH<100% space. A flat slope indicates that there was little loss of droplets as the diameter falls. Smaller droplets have greater surface area per volume, and a skilled artisan would expect greater surface area to encourage evaporation. A flat slope with ozone is consistent with little evaporation in a RH<100% space.

The enclosure 14 was modified to vary the distance between the nozzles 28,29. The cone angle of the nozzles 28,29 in this exemplary embodiment is 7°. The nozzle diameter is 0.5 in. A schematic illustration of what is believed to be occurring at different separations is given in FIGS. 4A-4C. At 12- (FIG. 4A), 24- (FIG. 4B), and 36-in. (FIG. 4C) separation, few light-dispersing droplets were formed. This is believed to be because, at the smaller distance, most of the droplets coalesce and fall down. At the larger distance, the droplets are diluted and blow by each other without creating a family of droplets<1 μm. At 24 in. (FIG. 4B), a doughnut of cloud dispersing small (<1-μm) droplets were observed surrounding the impingement point.

When the droplet size was measured, the ratio of the number median diameter (NMC) to the volume mean diameter (VMD) was measured. With 0.4 ppm ozone in the cloud, this ratio was 0.1330. Other with-ozone data points were similar.

The area of the impingement point is a function of the distance from the apex of the nozzle, since area=π×(distance+0.24 in.)×tan 7°)$^2$. At 12 in., the area=7.1 in.$^2$; at 24 in., 27.8 in.$^2$; at 36 in., 62.2 in.$^2$). The impinging velocity is inversely proportional to the area; so a spray from a 12-in. separation is 3.9 times faster than for 24 in.; for 36 in., it is half (0.45) the velocity of the 24-in. positioning. The 36-in. positioning separates the droplets so much that the probability of impinging is reduced. The velocity of the impingement is so violent at 12 in. that the droplets coalesce and fall to the enclosure wall. At 24 in., the velocity is just right to harvest light-reflecting droplets.

The ratio of NMD to VMD is a measure of the efficiency of creating small droplets. Only 13% of the volume of droplets were small or intermediate (<3.13 μm). Thus the impingement process is a very "inefficient" use of ozone.

The water 38 in the enclosure bottom 39 was captured and measured for dissolved ozone using known techniques. The standard test is to put a measured amount of reagent into a known volume of water and measure the ozone concentration by comparing the color to a chart after 60 sec.

Gas-phase ozone was varied from 0 to 4.2 ppm. At 60 sec there was no color change at all conditions, suggesting no ozone in the sump water; after 30 min the color change for the with-ozone samples suggested the ozone concentration was 0.6 ppm; after 20 h, the color change for the with-ozone samples suggested the ozone concentration was >2 ppm.

It is well known that the hydroxyl radical propagation step can regenerate oxidative compounds. It is speculated that the apparent increase of ozone over time is associated with a propagating radical mechanism. This observation directly contradicts all known prior art.

A nozzle of the above-cited '748 and '962 patents was set up to directly impinge on a series of inoculated stainless steel plates (e.g., methicillin-resistant *Staphylococcus aureus*, MRSA) at a variety of times and ozone concentrations. The results varied, but in all cases the log kill of targeted organisms was only about 2.

A nozzle of the above-cited '748 and '962 patents was also used to control relative humidity at <100%. A cloud was formed adjacent to the nozzle cone. Inoculated stainless steel plates were exposed to the cloud for various times and ozone concentrations. The results varied, but the log kill was about 4.

When droplets impinge on a surface, they coalesce and lose their internal, surface-tension-induced pressure. The hydroxyl radical propagating mechanism stops, and disinfection efficiency drops by four orders of magnitude (per Cho). When the plates were exposed to just the cloud, the hydroxyl activity was retained, and the disinfection efficiency increased.

The impinging nozzles 28,29 within the enclosure 14 were used to expose inoculated fresh strawberries in an enclosed space to the cloud 11. The ozone-in-gas was 4 ppm. The strawberries had a 6-log kill of the inoculated organism.

This experiment was replicated with inoculated Petri dishes in which the dishes were upside down, facing away from the nozzle, with one edge elevated ¼ in. These dishes had a 6-log kill.

The ozone cloud drifted over and around all the strawberries without wetting them. The pressure was retained inside the small droplets. The system 10 of the present invention increased the number of small droplets, increasing "C" in the CT equation. The log kill increased.

The upside down Petri agar would have been protected from intermediate-sized droplets. Small cloud droplets can move around physical impediments and directly contact the agar.

An ozone concentration of 4 ppm is that at which the pH drop came to equilibrium. This means the radical concentration per droplet was maximized. This also increased C in the CT equation. The CT equation is really $(C_{radical\ concentration\ per\ drop}+C_{number\ of\ drops})\times T_{exposure\ time})$.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details of construction and use.

Having now described the invention, the construction, the operation and use of preferred embodiments thereof, and the advantageous new and useful results obtained thereby, the new and useful constructions, and reasonable equivalents thereof obvious to those skilled in the art, are set forth in the appended claims.

What is claimed is:

1. A method for producing an ozone-containing disinfecting cloud comprising:

directing compressed gas, ozone, and water to a pair of atomizing nozzles having outlets positioned in opposed relation to each other;

producing a spray of ozonated water from the compressed gas, ozone, and water from the pair of atomizing nozzles;

directing the produced sprays toward each other, to form a cloud comprising droplets having a size distribution;

retaining droplets having a size greater than a predetermined limit; and expelling a portion of the cloud comprising droplets having a size less than the predetermined limit, the expelled cloud having a pH lower than a pH of retained droplets.

2. The method recited in claim 1, wherein the expelling step comprises directing air toward each of the atomizing nozzles using a pair of fans.

3. The method recited in claim 2, further comprising:

measuring a humidity within the expelled cloud;

comparing the received humidity measurement with a predetermined humidity value;

increasing a speed of the fans if the measured humidity is less than the predetermined humidity value; and decreasing the fan speed if the measured humidity is greater than the predetermined humidity value.

4. The method recited in claim 1, further comprising:

measuring an ozone concentration in the expelled cloud;

comparing the measured ozone concentration with a predetermined concentration value;

increasing an amount of the ozone directed to the nozzles if the measured concentration is less than the predetermined concentration value;

decreasing the amount of the ozone directed to the nozzles if the measured concentration is greater than the predetermined concentration value.

5. The method recited in claim 1, further comprising channeling the retained droplets to the pair of nozzles.

6. The method recited in claim 1, controlling a velocity of the compressed gas directed to the nozzles to a desired velocity.

7. The method recited in claim 1, wherein the predetermined limit of droplet size comprises approximately 1 μm.

8. A method for disinfecting a space comprising:

producing an ozone-containing disinfecting cloud by:

directing compressed gas, ozone, and water to a pair of atomizing nozzles having outlets positioned in opposed relation to each other; producing a spray of ozonated water from the compressed gas, ozone, and water from the pair of atomizing nozzles;

directing the produced sprays toward each other, to form a cloud comprising droplets having a size distribution; and expelling a portion of the cloud comprising droplets having a size less than a predetermined limit, the expelled cloud having a pH lower than a pH of retained droplets; and directing the produced cloud into an area desired to be disinfected.

* * * * *